(12) United States Patent
Arredondo et al.

(10) Patent No.: US 7,619,118 B2
(45) Date of Patent: *Nov. 17, 2009

(54) PROCESS FOR THE CONVERSION OF GLYCEROL TO PROPYLENE GLYCOL AND AMINO ALCOHOLS

(75) Inventors: Victor Manuel Arredondo, West Chester, OH (US); Patrick Joseph Corrigan, Glendale, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 217 days.

This patent is subject to a terminal disclaimer.

(21) Appl. No.: 11/810,776

(22) Filed: Jun. 7, 2007

(65) Prior Publication Data
US 2007/0287865 A1    Dec. 13, 2007

Related U.S. Application Data

(60) Provisional application No. 60/811,704, filed on Jun. 7, 2006.

(51) Int. Cl.
*C07C 209/24* (2006.01)
*C07C 209/26* (2006.01)
*C07C 209/28* (2006.01)
*C07C 27/04* (2006.01)

(52) U.S. Cl. .................. 564/471; 564/463; 564/472; 568/861

(58) Field of Classification Search .............. None
See application file for complete search history.

(56) References Cited

U.S. PATENT DOCUMENTS

| | | | |
|---|---|---|---|
| 4,105,669 A | 8/1978 | Himmele et al. | |
| 4,111,840 A | 9/1978 | Best | |
| 4,123,462 A | 10/1978 | Best | |
| 4,151,204 A | 4/1979 | Ichikawa et al. | |
| 4,642,394 A | 2/1987 | Che | |
| 4,942,266 A | 7/1990 | Fleckenstein et al. | |
| 4,982,020 A | 1/1991 | Carduck et al. | |
| 5,081,321 A | 1/1992 | Fukuhara et al. | |
| 5,214,219 A | 5/1993 | Casale et al. | |
| 5,276,181 A | 1/1994 | Casale et al. | |
| 5,288,911 A | 2/1994 | Koppenhoefer et al. | |
| 5,364,986 A | 11/1994 | Demmering et al. | |
| 5,387,720 A | 2/1995 | Neher et al. | |
| 5,426,249 A | 6/1995 | Haas et al. | |
| 5,536,879 A | 7/1996 | Antons et al. | |
| 5,616,817 A | 4/1997 | Schuster et al. | |
| 5,731,479 A | 3/1998 | Antons | |
| 6,057,442 A | 5/2000 | Wulff-Doring et al. | |
| 6,080,898 A | 6/2000 | Drent et al. | |
| 6,310,254 B1 | 10/2001 | Antons et al. | |
| 6,376,713 B1 | 4/2002 | Baiker et al. | |
| 6,479,713 B1 | 11/2002 | Werpy et al. | |
| 6,841,085 B2 | 1/2005 | Werpy et al. | |

2005/0244312 A1    11/2005    Suppes et al.

FOREIGN PATENT DOCUMENTS

| | | |
|---|---|---|
| CS | 209151 B1 | 11/1981 |
| DE | 41 28 692 A1 | 3/1993 |
| DE | 43 02 464 A1 | 8/1994 |
| GB | 428462 | 5/1935 |
| GB | 1 554 176 A | 10/1979 |
| JP | 01056662 | 3/1989 |
| WO | WO 93/05006 | 3/1993 |
| WO | WO 2005/095536 A2 | 10/2005 |
| WO | WO2007010299 | 1/2007 |

OTHER PUBLICATIONS

U.S. Appl. No. 11/810,778, filed Jun. 7, 2007, Arredondo et al.
U.S. Appl. No. 11/810,796, filed Jun. 7, 2007, Arredondo et al.
Abaco, Atsushi et al., "An Improved, Convenient Procedure for Reduction of Amino Acids to Aminoalcohols: Use of NaBH4-H2SO4," Tetrahedron Letters, 1992, vol. 33, No. 38, pp. 5517-5518.
Carberry, James, "Chemical and Catalytic Reaction Engineering," Dover Publications Inc., Mineola NY, 1973, pp. 406 and 520.
Chiu, Chuang-Wei et al., "Dehydration of Glycerol to Acetol via Catalystic Reactive Distillation," AIChE Journal, 2006, vol. 52, No. 10, pp. 3543-3548.
Dasari, Mohanprasad et al., "Low Pressure Hydrogenolysis of Glycerol to Propylene Glycol," Applied Catalysis A: General, 2005, vol. 28, pp. 225-231.
Gobolos, S., et al., "Reductive Amination of Acetone on Tin Modified Skeletal Nickel Catalysts," Heterogeneous Catalysis and Fine Chemicals II, Elsevier Science Publication, 1991, pp. 335-342.
Gomez, Silvia, et al., "The Reduction Amination of Aldehydes and Ketones and the Hydrogenation of Nitriles: Mechanistic Aspects and Selectivity Control," Adv. Synth. Catal., 2002, vol. 344, No. 10, pp. 1037-1057.
Gribble, Gordon W., et al., "Sodium Borohydride in Carboxylic Acid Media: A Phenomenal Reduction System," Chemical Society Reviews, 1998, vol. 27, pp. 395-404.

(Continued)

*Primary Examiner*—Brian J Davis
(74) *Attorney, Agent, or Firm*—Stephen T. Murphy; Kim William Zerby; Steven W. Miller

(57) ABSTRACT

Processes for the conversion of glycerol to a product mixture of an amino alcohol product and propylene glycol are disclosed. Glycerol is converted to hydroxyacetone and the hydroxyacetone is reduced with a reducing agent or reacted with an amine compound to give an adduct which is reduced using the reducing agent to obtain a product mixture of propylene glycol and an amino alcohol product.

29 Claims, 2 Drawing Sheets

OTHER PUBLICATIONS

Jere, Frank T., et al., "Stereoretentivie C-H Bond Activation in the Aqueous Phase Catalytic Hydrogenation of Amino Alcohols," Organic Letters, 2003, vol. 5, No. 4, pp. 527-530.

McKennon, Marc J., et al., "A Convenient Reduction of Amino Acids and Their Derivatives," Journal of Organic Chemistry, 1993, vol. 58, pp. 3568-3571.

Nishimura et al., "Handbook of Heterogeneous Catalytic Hydrogenation for Organic Synthesis," Wiley & Sons, 2001, Chapter 6, pp. 226-253.

Nishimura et al., "Handbook of Heterogeneous Catalytic Hydrogenation for Organic Synthesis," Wiley & Sons, 2001, Chapter 8, pp. 286-314.

PROCESS FOR THE CONVERSION OF GLYCEROL TO PROPYLENE GLYCOL AND AMINO ALCOHOLS

CROSS REFERENCED TO RELATED APPLICATIONS

This application claims the benefit of U.S. Provisional Application No. 60/811,704, filed Jun. 7, 2006, the disclosure of which is incorporated in its entirety by reference herein.

FIELD OF THE INVENTION

Embodiments described herein relate generally to process for the production of products comprising propylene glycol and an amino alcohol from glycerol.

BACKGROUND OF THE INVENTION

Some amino alcohols may be represented by the general formula:

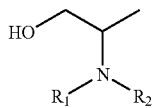

These amino alcohols can be valuable materials because they may be used as solvents, intermediates for making surface active agents, corrosion inhibitors in metal working fluids, neutralizing agents in acid scrubbing during natural gas or syngas purification processes, and aids in the preparation of compounds for use in the pharmaceutical industry.

Currently, processes exist for the preparation of amino alcohols, such as amino alcohols with the general formula set forth herein. Such processes can involve reacting polyhydroxy compounds, such as ethylene glycol, 1,2-diols, 1,3-diols, and polyglycols, with amine compounds and hydrogen in the presence of a heterogeneous catalyst. One concern with such processes is that they can exhibit poor-to-moderate conversions and selectivities. This undesired outcome can result from the fact that the reactions can yield complex product mixtures consisting of amino alcohols, di- and tri-amines, oligomeric polyamines, cyclic amines (e.g. pyrrolidines, piperidines, and piperazines), unreacted starting materials and other unidentified compounds. Examples of these catalysts and processes can be found in U.S. Pat. Nos. 6,376,713; 6,057,442; 5,288,911; 4,123,462; 4,151,204; and 4,111,840.

Alternately, amino alcohols can be prepared by reacting an amine compound with 2-chloro-1-propanol (see, for example, JP 01056652) or by stoichiometric reduction of the corresponding amino acids and ester derivatives with a variety of reducing reagents (A. Abiko et al., Tetrahedron Lett. 1992, 33, 5517; M. J. McKennon, et al., J. Org. Chem. 1993, 58, 3568, and references therein) and by catalytic hydrogenation of amino acids, for example as reported in U.S. Pat. Nos. 5,536,879; 5,731,479; and 6,310,254. In works described by Miller, et al., (Organic Letters, 2003, 5(4), 527) on the conversion of alanine to desired products it is stressed the importance of performing hydrogenations at low pH such that the amino acid is in the protonated form rather than carboxylate form. In general, the catalytic hydrogenation of amino acids require a low solution pH in conjunction with high catalyst loading, prolonged reaction times, and high hydrogen pressure. Thus, these processes can often be costly since additional expensive feedstocks and reagents are needed.

Propylene glycol, also known as 1,2-propanediol, is a major industrial chemical with a variety of end uses. More than 400 million kilograms of propylene glycol are consumed within the United States per year. One major end use of propylene glycol is as a raw material in the manufacture of polyester resins. Propylene glycol is also used in cosmetics, personal care products, pharmaceuticals, and food applications, at least in part due to its low toxicity, absence of color and odor, excellent solvent characteristics, and good emollient properties. The United States Food and Drug Administration has determined propylene glycol to be "generally recognized as safe" (GRAS) for use in foods, cosmetics, and medicine. Other categories of use include applications as functional fluids, such as aircraft de-icing fluids, antifreezes, lubricants, inks, and heat transfer fluids, paints and coatings, plasticizers, and cellophane. Propylene glycol may also be used as a solvent and/or enzyme stabilizer in detergent applications.

Propylene glycol is commonly produced by the hydration of propylene oxide, which in turn, may be produced from propylene from petrochemical sources such as coal gas or cracking of petroleum. Thus, a large amount of propylene glycol is derived from non-renewable petroleum-based sources. Further, mixtures comprising propylene glycol and a 2-amino-1-propanol may have various uses in certain industrial processes and commercial products.

The industrial production of chemicals may be driven by economic concerns. Industrial scale production of certain chemicals requires large plant operations, oftentimes with equipment and reactors dedicated to the production of a specific chemical product. Decreasing the industrial infrastructure necessary for the production of various chemicals may result in an economic advantage to the company. For example, if a company could use specific infrastructural facilities for the production of multiple chemical end products, certain cost benefits may be realized.

Therefore, there remains a need for processes for producing a product comprising an amino alcohol and propylene glycol from inexpensive and renewable feedstocks, such as glycerol, in a cost effective manner, which can also reduce or eliminate the production of substantial amounts of undesired byproducts.

SUMMARY OF THE INVENTION

Embodiments of the present disclosure generally relate to a process for the simultaneous production of an amino alcohol and propylene glycol from a glycerol feedstock.

In one exemplary embodiment, the processes of the present disclosure generally relate to a process for converting glycerol to a product mixture comprising propylene glycol and an amino alcohol product. The process comprises reacting glycerol with a metal catalyst to obtain hydroxyacetone and reacting the hydroxyacetone with a reducing agent or an amine compound and the reducing agent to obtain a product mixture comprising propylene glycol and the amino alcohol product.

In another exemplary embodiment, the processes of the present disclosure generally relate to a process for converting glycerol to a product mixture comprising propylene glycol and a 2-amino-1-propanol. The process comprises reacting glycerol with a metal catalyst in a first reactor to obtain hydroxyacetone and reacting the hydroxyacetone with a reducing agent or an amine compound and the reducing agent to obtain a product mixture comprising propylene glycol and a 2-amino-1-propanol. According to the processes, reacting the hydroxyacetone comprises: reducing a first portion of the hydroxyacetone in a reactor with the reducing agent to produce the propylene glycol in the product mixture and reacting a second portion of the hydroxyacetone in the reactor with the amine compound to produce an adduct and reducing the adduct with the reducing agent in the reactor to produce the 2-amino-1-propanol in the product mixture.

In yet another exemplary embodiment, the processes of the present disclosure generally relate to a process for converting glycerol to a product mixture comprising propylene glycol and an amino alcohol compound having the formula:

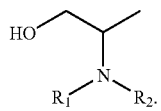

The process comprises reacting glycerol with a metal catalyst in a first reactor to obtain hydroxyacetone and reacting the hydroxyacetone with a reducing agent or an amine compound and the reducing agent to obtain a product mixture comprising propylene glycol and an amino alcohol compound. According to the processes, reacting the hydroxyacetone comprises: reducing a first portion of the hydroxyacetone in a reactor with the reducing agent to produce the propylene glycol in the product mixture and reacting a second portion of the hydroxyacetone in the reactor with the amine compound to produce an adduct and reducing the adduct with the reducing agent in the reactor to produce the amino alcohol in the product mixture. The amino alcohol has a formula where $R_1$ and $R_2$ of the amino alcohol are independent of one another and are selected from the group consisting of H, $C_1$-$C_{20}$ alkyl, $C_3$-$C_{20}$ cycloalkyl, $C_1$-$C_{20}$ hydroxyalkyl, aryl, $C_7$-$C_{20}$ alkyl-aryl, $C_7$-$C_{20}$ aryl-alkyl, and mixtures thereof, or $R_1$ and $R_2$ come together with the nitrogen to form a heterocyclic ring having from 5 to 7 ring atoms.

BRIEF DESCRIPTION OF THE DRAWINGS

The various embodiments of the Description of the Invention will be better understood when read in conjunction with the following drawings, wherein.

DETAILED DESCRIPTION OF THE INVENTION

A. Definitions

Figure 1:
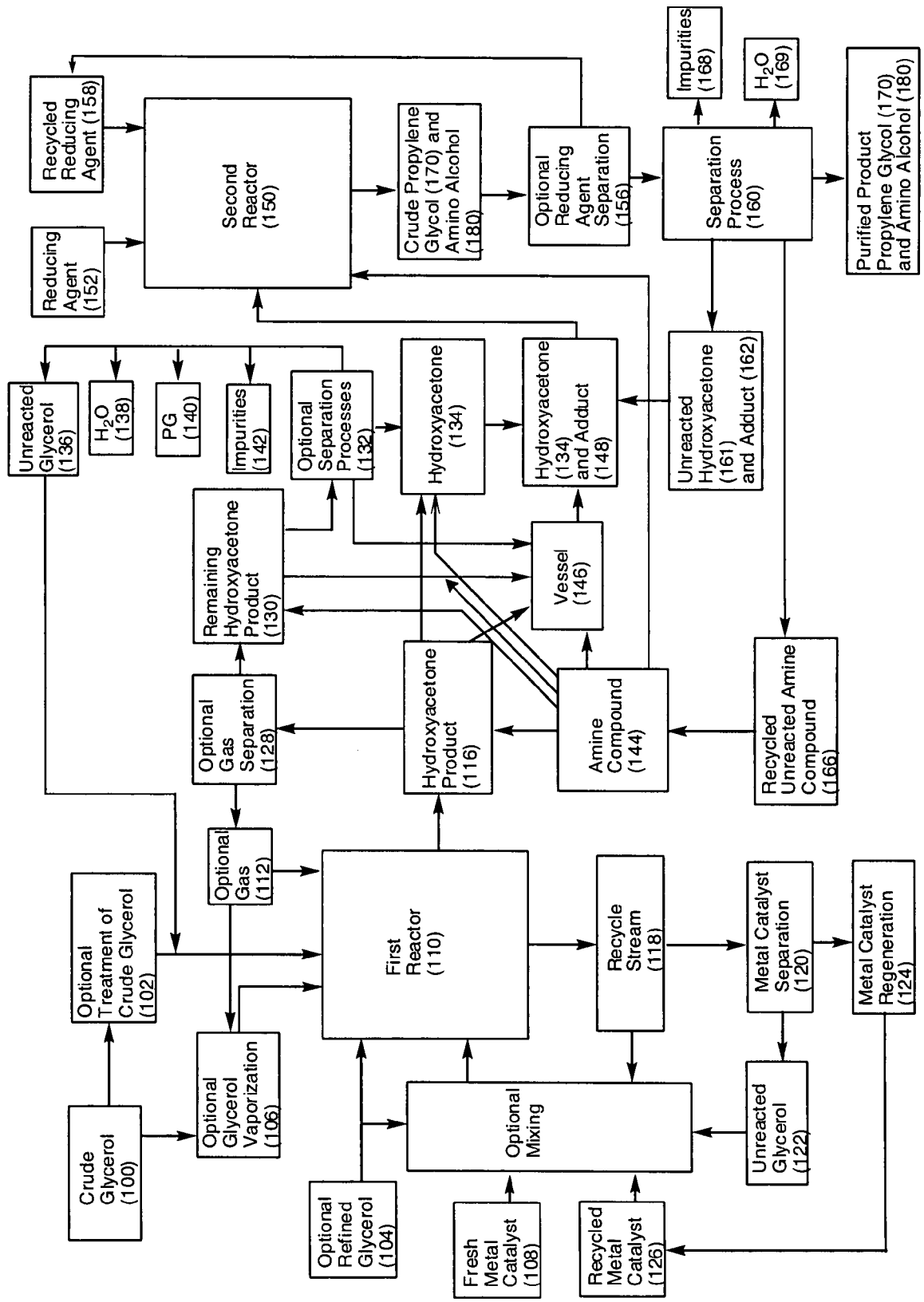
FIG. 1 illustrates a schematic flowchart representing an exemplary embodiment of a multiple stage process in accordance with the present disclosure.

As used herein, the term "comprising" means the various components, ingredients, or steps, which can be conjointly employed in practicing the various embodiments of the present disclosure. Accordingly, the term "comprising" encompasses the more restrictive terms "consisting essentially of" and "consisting of".

As used herein, the term "adduct" means any chemical species formed by the combination or condensation of two or more substances, such as hydroxyacetone and an amine compound.

As used herein, the term "crude glycerol" refers to glycerol that may contain impurities, including, but not limited to, water, inorganic salts such as chloride, sulfate, phosphate, acetate salts and others, organic compounds such as fatty acids, fatty esters, mono-glycerides, di-glycerides, phospholipids, protein residues, methanol, acids, bases, or combinations of any thereof. Impurities may account for from about 10% to about 50% of the crude glycerol, by weight.

As used herein, the term "reaction components" generally refers to chemical species that take part in a chemical transformation, for example, but not limited to, solvents, reactants, and catalysts. In addition, "reaction components" may include a gas, liquid, or solid or a reaction component dissolved in a solvent.

As used herein, the term "reducing agent" refers to any element, compound, or combination of elements and/or compounds that reduces another species by either increasing the hydrogen content or decreasing the oxygen content of the other species.

As used herein, the term "RANEY®" when used in conjunction with a metal catalyst means a catalyst that has been treated by a process that activates the catalyst, such as by reacting the catalyst with a second metal, such as aluminum, and/or by increasing the surface area of the catalyst. For example a RANEY® metal is a solid catalyst composed of fine grains of a metal-aluminum allow, produced when a block of the alloy is treated with concentrated sodium hydroxide to activate the catalyst. The activated catalyst has a porous structure with a high surface area. RANEY® is a registered trademark of W.R. Grace and Company, New York, New York. Other suitable catalysts that may be used in place of a RANEY® catalyst include skeletal catalysts and/or sponge metal catalysts.

As used herein, the term "glycerol" may refer to any of crude, treated, or refined glycerol as described herein, unless the glycerol is specifically designated as being crude, treated, or refined.

As used herein, the term "refined glycerol" means glycerol that is at least about 99% pure (i.e. containing less than about 1% impurities, such as those impurities described herein).

As used herein, the term "treated glycerol" means glycerol that has undergone at least one treating process such that the treated glycerol comprises greater than about 1% to about 10% impurities, such as those impurities described herein.

As used herein, the term "treating" means removing at least a portion of the impurities from the crude glycerol. "Treating" may be accomplished by a variety of methods, including, but not limited to neutralization, precipitation, filtration, evaporation, steam stripping, ion-exchange, adsorption, membrane separation, such as microfiltration, nanofiltration, osmosis and reverse osmosis, electro-deionization, and combinations of any thereof.

All percentages disclosed herein are by weight unless otherwise specified.

B. Processes

Various embodiments of the present disclosure relate generally to a process for converting glycerol to a product mixture comprising propylene glycol and an amino alcohol product. More specifically, certain embodiments herein disclose a process comprising reacting glycerol with a metal catalyst to obtain hydroxyacetone in a first step and in a second step reacting the hydroxyacetone with a reducing agent or reacting the hydroxyacetone with an amine compound and the reducing agent to obtain a product mixture comprising propylene glycol and an amino alcohol product. The process may be represented by the following chemical equation:

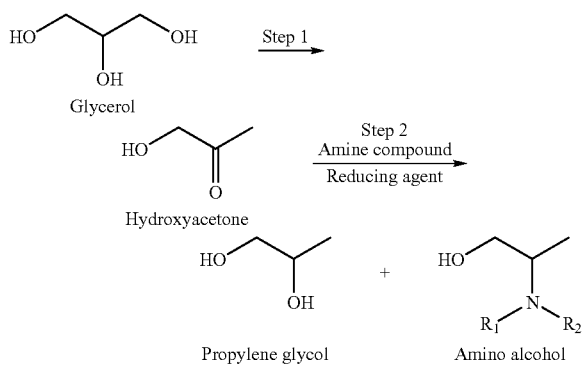

According to other embodiments, the process may be a one step process in which the conversion of glycerol to hydroxyacetone and the conversion of the hydroxyacetone to the product mixture comprising propylene glycol and the amino alcohol may occur in a single reaction process (one-pot or single reactor). Variations of such processes will become clear from the following description.

For example, according to the processes described herein, glycerol is reacted with a metal catalyst to produce hydroxyacetone and a first portion of the hydroxyacetone is directly reduced with the reducing agent to produce the propylene glycol in the product mixture and a second portion of the hydroxyacetone is reacted with the amine compound to form an adduct which is then reduced with the reducing agent to produce the amino alcohol compound in the product mixture. The product mixture comprising propylene glycol and the amino alcohol may be used directly in certain industrial processes and commercial products, or, alternatively, may be separated into its propylene glycol and amino alcohol components by a separation process. Variations of such processes will become clear from the following description.

According to various embodiments, the processes described herein involve reacting glycerol with a metal catalyst to obtain a product comprising hydroxyacetone in a first step. According to certain embodiments, the product hydroxyacetone may further comprise other components, such as, for example, unreacted glycerol, water, propylene glycol and other impurities. Glycerol acceptable for use herein may be liquid crude, treated or refined glycerol, or crude glycerol vapor, as described in greater detail herein. Referring to FIG. 1, crude glycerol (100) may contain impurities, including, but not limited to, water, inorganic salts, such as chloride, sulfate, phosphate, acetate salts and others, organic compounds such as fatty acids, fatty ester, monoglycerides, di-glycerides, phospholipids, protein residues, methanol, acids, bases and various combinations of any of these impurities. In certain embodiments of the crude glycerol, impurities may account for at least about 10% of the crude glycerol, and in specific embodiments from about 10% to about 50% of the crude glycerol, by weight. In other embodiments, the crude glycerol may comprise less than 10% impurities, such as from 1% to 10% impurities. It will be understood by one skilled in the art that the amount of impurities in the crude glycerol may vary according to the method of production and that in certain more efficient processes, the crude, untreated, glycerol may contain lower levels of impurities that the crude glycerol from other processes. The purity of the "crude" glycerol used in the reaction should not be viewed as limiting herein. According to certain embodiments, the crude glycerol may be obtained in the course of an industrial process, such as, during the production of biodiesel, or from the conversion of fats/oils of plant or animal origin through saponification, trans-esterification or hydrolysis reactions. As described herein, in certain conventional processes, crude glycerol must first be refined prior to use in order to facilitate process control, maximize process yields, avoid catalyst poisoning, and/or reduce impurities in the final reaction product. Because such refining processes can be costly, in certain embodiments of the processes herein, it may be more desirable to use the crude glycerol directly or with minimal processing, treating, or purification. Various embodiments described herein may address this issue by providing more cost-effective processes that allow for the use of crude glycerol without refinement or treating the glycerol.

Although certain embodiments of the present disclosure generally focus on the use of crude glycerol, the processes of the present disclosure are not limited to the use of crude glycerol. For example, in another embodiment, crude glycerol may be optionally treated (102) prior to use in the processes described herein. Treating the crude glycerol may aid in reducing the amount of impurities present in the glycerol, without necessarily having to fully refine the crude glycerol. According to these embodiments, treating the crude glycerol may result in significant cost savings compared to refining the crude glycerol. As used herein, "treating," crude glycerol may be accomplished by a variety of methods, including, but not limited to neutralization, precipitation, filtration, evaporation, steam stripping, ion-exchange, adsorption, membrane separation, such as microfiltration, nanofiltration, osmosis and reverse osmosis, electro-deionization, and combinations of any thereof. Those skilled in the art will understand how the treatment of crude glycerol may be accomplished via the various methods set forth herein, and that such treatment may vary depending on the nature and amount of impurities present in the crude glycerol. Regardless of which treatment method is employed, the resulting "treated glycerol" may comprise from about 1% to about 10% of one or more of the aforementioned impurities by weight. The reduction in impurities in the treated glycerol may help provide better reaction yields during the processes described herein.

According to other embodiments, refined glycerol (104) having greater than about 99% purity may be used in the processes described herein. The glycerol may be refined according to any refinement method known in the art. In various embodiments, the refined, treated, or crude glycerol may be neat or diluted with a polar solvent (e.g. water or an alcohol). Various mixtures of refined, treated and/or crude glycerol may also be suitable for use in various embodiments disclosed herein.

Alternately, according to other embodiments, the crude glycerol may be vaporized (106) prior to submitting the glycerol to the processes described herein. As vapor phase reactions can be faster than liquid phase reactions, glycerol vapor may be desired such that the first portion of the process may be conducted in the vapor phase, for example, to speed up the rate of the reaction. Vaporization of the glycerol may be carried out using any vaporizer known to those skilled in the art including, but not limited to, a flash tank evaporator or a wiped film evaporator. One skilled in the art would recognize that the conditions of temperature and pressure may vary according to the vaporization equipment used. An additional benefit of vaporizing the crude glycerol is that glycerol vaporization may reduce the amount of impurities present in the crude glycerol without having to fully refine the glycerol. In this way, using glycerol vapor may be a more cost effective option than using refined glycerol. As used herein, the term "glycerol" shall include crude, treated, or refined glycerol except where the glycerol has been specifically designated as crude, treated, or refined.

A metal catalyst (108) may also be provided to react with the glycerol to produce hydroxyacetone. According to various embodiments, any metal catalyst having active sites comprising one or more transition element metals may be used herein. For example, according to certain embodiments, the metal catalyst may include, but are not limited to, copper, chromium, nickel, zinc, cobalt, manganese, silicon, aluminum, oxides thereof, and combinations of any thereof. According to one embodiment, the metal catalyst may be a copper chromite catalyst (also known in the art as a copper-chromium oxide catalyst) that may comprise from about 20% to about 75% copper oxide and from about 20% to about 75% chromium trioxide. According to another embodiment the catalyst may be a copper zinc catalyst. Additionally, the metal catalyst, for example, the copper chromite catalyst or the copper zinc catalyst, may contain small amounts of stabilizers, such as barium oxide. In certain embodiments, the metal catalyst may also be promoted with one or more metal oxides including, but not limited to, oxides of magnesium, calcium, barium, manganese, molybdenum or silicon, which may help render the metal catalyst more active and/or more stable. Moreover, in certain embodiments, the metal catalyst may be used fresh (i.e. the oxide form) or it may be reduced in a stream of hydrogen prior to use. According to certain embodiments, the use of a reduced catalyst may be desired for various reasons. For example, in certain embodiments, using a reduced catalyst may produce hydroxyacetone more rapidly and with fewer impurities and, in other embodiments, using a reduced catalyst may contribute to a longer catalyst lifetime due to resistance to catalyst poisoning and/or degradation.

According to various embodiments, reacting the glycerol with the metal catalyst may occur in a first reactor (110), optionally in the presence of a gas (112), in a slurry mode or a fixed bed mode. Any reactor known to those skilled in the art may be used herein and may include a batch reactor, a stirred tank reactor, a semi-batch reactor, a continuous reactor, a continuous stirred tank reactor, a slurry reactor, a fixed bed reactor, a tubular reactor, a column reactor, a packed bed reactor, a fluidized bed reactor, a trickle bed reactor, a membrane reactor, a plate and frame reactor, a Carberry-type reactor (also called the "Notre Dame reactor, see, J. J. Carberry, "Chemical and Catalytic Reaction Engineering," Dover Publications, Inc. Mineola, N.Y., 1976, p. 406, see also p. 520 for an illustration of various reactor types suitable for use in the present disclosure, the disclosure of which in incorporated in its entirety by reference herein), a plug flow reactor, and a reactive distillation, or various combinations of any thereof. It will be understood that the manner in which the glycerol and metal catalyst are fed/added into the reactor can vary depending on the equipment used and the phase of each reaction component. It will be understood that the manner in which the glycerol and metal catalyst are fed/added into the reactor can vary depending on the equipment used and the phase of each reaction component. However, in those embodiments in which glycerol vapor is used, one skilled in the art will understand that it may be more advantageous to have the metal catalyst already in place in the first reactor prior to the addition of the glycerol vapor since it may simplify the process of contacting the glycerol vapor with the metal catalyst.

While the amount of metal catalyst may vary, in one embodiment, the amount may be from about 0.01% to about 100%, and in another embodiment from about 0.01% to about 5% by weight, relative to glycerol, for example in a slurry type reactor. For other reactors, such as continuous reactor, for example a fixed bed reactor (including trickle bed reactors), the catalyst loading of the reactor may vary and may depend on the bed reactor design, such as the bed volume of the reactor and/or the reactant flow rate. One skilled in the art will recognize that the amount of metal catalyst used can vary depending on the type of reactor used and the desired speed of the reaction. For example, faster reactions can be advantageous because they generally allow for the use of more compact reaction equipment and can result in the formation of fewer byproducts, while slower reactions can be advantageous because they can often be carried out using less catalyst, which can lead to lower operating costs. In certain embodiments, where a faster reaction rate may be desired, the amount of metal catalyst may be increased.

According to certain embodiments, reacting the glycerol with the metal catalyst may occur under gas sparging. If a gas (112) is used, any gas known to those skilled in the art may be acceptable for use herein. Examples of gasses that may be useful in certain embodiments of the present processes can include the noble gases (e.g. helium or argon), nitrogen, carbon dioxide, superheated steam, and combinations of any thereof. In certain embodiments, the gas may comprise nitrogen. Without being limited by theory, it is believed that the inclusion of a gas, in combination with the reaction temperature, can be beneficial because it can improve reaction yields and selectivities by reducing contact time between the catalyst and the hydroxyacetone product by continually aiding in the removal of the hydroxyacetone and water from the reaction mixture as a vapor. For example, as the hydroxyacetone product is formed under the reaction conditions and temperature, it may be vaporized and the hydroxyacetone vapor transmitted out of the reactor by the gas stream. This in turn can prevent the hydroxyacetone from further reacting with the metal catalyst and generating undesired byproducts.

According to one specific embodiment, the first reactor (110) may be a trickle bed reactor. The trickle bed reactor may comprise at least one packed column, wherein the column is packed with the metal catalyst. In certain embodiments, the trickle bed reactor may comprise a plurality of columns, such as, for example, from 2 to 10 columns, arranged in series or in parallel. One skilled in the art would recognize that the number of columns in the trickle bed reactor may vary according to the required reaction time, the flow rate of the process, and/or the height, total bed volume, or catalyst loading of the column. In the trickle bed reactor for the conversion of glycerol to hydroxyacetone, liquid glycerol feed is fed into the reactor at a low flow so that a thin layer of liquid may form over at least a portion of the surface of the metal catalyst particles that are packed into the column. In certain embodiments, the space between the catalyst particles may be fed with the gas (112), such that as the glycerol is converted to the hydroxyacetone product (116), the hydroxyacetone product is volatilized and the hydroxyacetone vapor carried from the reactor by the gas. One skilled in the art will recognize that the number of columns in the trickle bed reactor may vary according to a variety of factors, including, but not limited to, the reactivity of the metal catalyst, the size and/or packing volume of the individual columns, the purity of the glycerol reactant, and the reaction conditions (such as reaction temperature).

Regardless of the manner of introduction of the various reaction components, once inside the first reactor, the glycerol and metal catalyst may react, in the presence of the gas if included, to produce a hydroxyacetone product that, in addition to hydroxyacetone, may comprise any of unreacted glycerol, water, propylene glycol, and other impurities. While not intending to be limited by theory, it is believed that hydroxyacetone may be formed via a combination of dehydrogenation and dehydration reactions. More specifically, glycerol may be first dehydrogenated to glyceraldehyde in equilibrium with its enolic tautomer. The primary hydroxyl group of this enolic tautomer may then interact with the acidic site present in the chromium oxide, thereby catalyzing the loss of water (dehydration) with concomitant rearrangement of the double bond to yield hydroxyacetone. Alternately, a primary hydroxyl group of the glycerol may strongly interact with an acid site on the catalyst to facilitate the loss of water and yield hydroxyacetone via its enolic tautomer.

In view of the above, it will be understood that reaction conditions can vary depending on the particular reaction components (i.e. glycerol, metal catalyst and gas, if present) and reactor type selected. In certain embodiments reacting the glycerol with the metal catalyst may occur at a temperature of from about 160° C. to about 300° C., and in another embodiment from about 200° C. to about 240° C. According to certain embodiments, reacting the glycerol with the metal catalyst may occur at about atmospheric pressure, although pressures above and below atmospheric pressure, for example, for example in one embodiment, pressures from about 0.1 bar to about 60 bar may be used herein and in another embodiment, pressures from about 0.1 bar to about 10 bar, may be used herein. Similarly, the time needed to carry out the reaction can vary depending on the reaction components used, for example, in one embodiment the reaction may be carried out for from about 1 minute to about 24 hours, as measured by the residence time in the reactor, for example when the glycerol is in the liquid phase. In other embodiments where the glycerol is in a vapor phase, the reaction time may be from about 1 second to about 1 hour. Those skilled in the art will understand how to select the proper process parameters based on such factors as the reaction components and equipment used.

Once the reaction between the glycerol and metal catalyst occurs, a hydroxyacetone product (116), as well as a recycle stream (118) may be obtained. As used herein, "hydroxyacetone product" means the composition(s) resulting from, or remaining after, reacting the glycerol with the metal catalyst, optionally in the presence of the inert gas, for example in the first reactor. While it should not be limited to such, the hydroxyacetone product may be in the vapor phase (which may be condensed prior to the next step in the process). In addition to hydroxyacetone, the hydroxyacetone product may further comprise any of unreacted glycerol, propylene glycol, water, impurities and combinations of any thereof. The hydroxyacetone product may also comprise any gas (112) if used in the reaction.

The recycle stream (118) may generally be in the liquid phase and may comprise the metal catalyst, and/or unreacted glycerol, as well as high boiling point impurities. In one embodiment, the recycle stream (118) may be recycled directly back to the first reactor (110) for reuse. In another embodiment, the metal catalyst in the recycle stream (118) may be partially or completely separated (120) and the remaining unreacted glycerol (122) (and any impurities present) may be recycled back to the reactor (110). In certain embodiments, the separated metal catalyst may then be regenerated (124), since it may lose at least a portion of its activity over time, prior to being recycled (126) to the first reactor for reuse. Optionally, the recycled metal catalyst (126), whether regenerated or not, may be mixed with fresh metal catalyst (108) and/or unreacted glycerol (122) and then added back into the first reactor (110) to replace at least a portion of the used/removed reaction components.

Similarly, when handling the hydroxyacetone product (116), the gas (if used) may be optionally separated (128) from the remaining hydroxyacetone product (130) and recycled back to the first reactor (110) for reuse. The remaining hydroxyacetone product (130), which as previously mentioned, may comprise hydroxyacetone, as well as, in certain embodiments, any of unreacted glycerol, water, propylene glycol and impurities, such as 1,3-dimethanol-p-dioxane and (2,4-dimethyl-1,3-dixolan-2-yl)methanol, may be further separated if desired (132) to isolate the hydroxyacetone (134) from the unreacted glycerol (136), water (138), propylene glycol (140) and impurities (142). Water (138) and impurities (142) may generally be recycled or discarded, while any propylene glycol (140) may be collected for use in other applications or mixed with the product mixture from the overall process, and any unreacted glycerol (136) may be recycled back for use as a reaction component for the first step of the process. The hydroxyacetone (134) may be added to a second reactor (150) for further processing.

According to the various embodiments, the processes described herein comprise reacting the hydroxyacetone with a reducing agent (152) or an amine compound (144) and the reducing agent (152) to obtain a product mixture comprising propylene glycol (170) and an amino alcohol product (180). Reacting the hydroxyacetone may occur in a reactor, such as either the first reactor (110, as described herein) or a second reactor (150). Further, reacting the hydroxyacetone may comprise directly reducing a first portion of the hydroxyacetone with the reducing agent (152) in the reactor to produce the propylene glycol (170) in the product mixture and reacting a second portion of the hydroxyacetone with the amine compound (144) to produce an adduct (148) and then reducing the adduct (148) with the reducing agent (152) in the reactor to produce the amino alcohol product (180) in the product mixture. As used herein, the term "portion" when used in reference to the hydroxyacetone from the first step of the process means a portion of the hydroxyacetone in the hydroxyacetone produced in the first step. The various portions of the hydroxyacetone are not separated from the other portions of the hydroxyacetone in the hydroxyacetone product. The hydroxyacetone may be the hydroxyacetone product (116), the hydroxyacetone product after gas separation (130) or the hydroxyacetone (134) after the separation processes (132).

As disclosed herein according to certain embodiments, reacting the hydroxyacetone with the reducing agent to produce the propylene glycol in the product mixture may comprise reducing a first portion of the hydroxyacetone with the reducing agent to produce the propylene glycol in the product mixture. According to certain embodiments, the first portion of the hydroxyacetone may comprise from about 0.01% to about 99.99% by weight of the hydroxyacetone produced in the first step of the process. In another embodiment, the first portion of hydroxyacetone may comprise from about 15% to about 85% of the hydroxyacetone produced in the first step of the process.

According to certain embodiments, hydroxyacetone may also react with the amine compound (144) to obtain the adduct (148), and the adduct (148) may be reduced with the reducing agent (152) to produce the amino alcohol product in the product mixture. For example according to certain embodiments, reacting the hydroxyacetone may comprise reacting a second portion of the hydroxyacetone with the amine compound to produce the adduct and then reducing the adduct with the reducing agent in a reactor to produce the amino alcohol product in the product mixture. According to certain embodiments, the second portion of the hydroxyacetone may comprise from about 0.01% to about 99.99% by weight of the hydroxyacetone produced in the first step of the process. In another embodiment, the second portion of hydroxyacetone may comprise from about 15% to about 85% of the hydroxyacetone produced in the first step of the process.

According to various embodiments, reacting the hydroxyacetone with the amine compound, such as reacting a second portion of the hydroxyacetone with the amine compound, may be performed by a variety of processes. For example, according to one embodiment, the amine compound may be added to the hydroxyacetone in the hydroxyacetone feed stream going from the first reactor (110) to the second reactor (150). For example, the amine compound may be added to the hydroxyacetone feed stream as the hydroxyacetone (or hydroxyacetone product) is transferred from the first reactor (110) to the second reactor(150), while the hydroxyacetone product is being separated from the gas (112), during the process to separate the hydroxyacetone from the hydroxyacetone product (i.e., separating the hydroxyacetone from one or more of unreacted glycerol, water, propylene glycol, and impurities (132)), or in a feed stream between any these processes. In another embodiment, the amine compound may be added to the hydroxyacetone (or hydroxyacetone product) in an intermediate vessel (146) between the first reactor (110) and the second reactor (150). In another embodiment, the amine compound may be added to the hydroxyacetone (or hydroxyacetone product) in the second reactor (150).

According to certain embodiments, the amine compound (144) may be a compound selected from the group consisting of ammonia, ammonium hydroxide, hydroxylamine, primary amines, secondary amines, alkanolamines, and combinations of any thereof. In one embodiment, the amine compound may be ammonia, while in another embodiment, the amine compound may be ammonium hydroxide. In another embodiment, the amine compound may be hydroxylamine. One having skill in the art, based on the disclosure herein, will understand that selection of the appropriate amine compound will depend on the structure of the desired amino alcohol product. For example, in certain embodiments where a primary amino alcohol product is desired, an amine compound such as ammonia (gaseous or liquid) or ammonium hydroxide would be selected, whereas a secondary amino alcohol product or a tertiary amino alcohol product would utilize a primary amine compound or secondary amine compound, respectively.

In certain embodiments, reacting the hydroxyacetone (for example, the second portion of the hydroxyacetone) with the amine compound to obtain the adduct may further comprise optionally adding an acid catalyst to the hydroxyacetone and the amine compound. For example, in certain embodiments, the rate of the reaction between the hydroxyacetone and the amine compound may be increased by addition of an acid catalyst, such as, for example, a Brønsted-Lowry acid, a Lewis Acid, or combinations of any thereof. Those skilled in the art will understand how to select an acid catalyst, such as a solid acid catalyst, based on such factors as equipment and cost parameters. Some exemplary solid acid catalysts acceptable for use herein may include metal oxides or metal mixed oxides of the elements Zr, Ti, Mo, W, Fe, B, Al and Si; zeolites, metal or ammonium salts of mineral acids such as hydrochloric acid, sulfuric acid, nitric acid, phosphoric acid, or organic acids such as formic acid, acetic acid and sulfonic acids; cross-linked sulfonated polystyrene ion exchange resins such as AMBERLYST™ (Rohm & Haas, USA, PA), polyperfluorosulfonic acid resin such as NAFION® (Dupont, USA, Delaware), with or without silica nanocomposite; kieselguhr, alumina, titania or clays impregnated with a strong acid. While not intending to be limited by any particular mechanism, it is believed that the acid catalyst may activate the carbonyl of the hydroxyacetone toward nucleophilic attack by the amine compound. The acid catalyst may be added to the hydroxyacetone prior to, concomitant with, or after the addition of the amine compound. In another embodiment, a mixture of the hydroxyacetone and the amine compound may be passed over or through an acidic resin. In other embodiments, acid catalysis may not be necessary since the amine compound may directly react with the hydroxyacetone to produce the adduct.

According to various embodiment, reacting hydroxyacetone (for example, the second portion of hydroxyacetone) with the amine compound to obtain the adduct may be done at any temperature effective to cause the reaction between the amine compound and the hydroxyacetone. For example, in certain embodiments, the reaction of the amine compound with the hydroxyacetone at a temperature ranging from about −20° C. to about 150° C. In other embodiments, the reaction between the hydroxyacetone and the amine compound may be occur at a temperature of from about −20° C. to about 70° C., and in another embodiment from about −10° C. to about 15° C. The reaction of the hydroxyacetone and the amine compound may occur at pressures of from about 1 bar to about 200 bar, and in one embodiment from about 1 bar to about 100 bar. In certain embodiments, the amine compound may be added to excess hydroxyacetone, that is molar ratio of amine compound to hydroxyacetone (total) may be from 0.01:1 to 0.99:1. In certain embodiments, depending on the reactivity of the hydroxyacetone with the amine compound, the amine compound may be in excess, with the molar ratio of the amine compound to hydroxyacetone being from about 1:1 to about 10:1, and in one embodiment from about 2:1 to about 4:1. The reaction may be carried out for from about 1 minute to about 3 hours and in one embodiment from about 15 minutes to about 90 minutes. One skilled in the art will understand how the reaction time may vary depending on the reaction conditions, reactivity of the amine compound, the presence of a catalyst, and/or equipment used.

As previously described, reacting hydroxyacetone (such as the second portion of the hydroxyacetone) and the amine compound produces an adduct (148). As used herein, "adduct" refers to any chemical species formed by combination or condensation of two or more substances. According to various embodiments, the two substances used to form the adduct may be hydroxyacetone (such as 116, 130, or 134) and the amine compound (144). The reaction of a carbonyl-containing compound, such as hydroxyacetone, with an amine to form an adduct that is subsequently reduced is known as reductive amination. The reductive amination of aldehyde or ketone-containing compounds may proceed in several steps and by various mechanisms depending on the structure of the reactants and the reaction conditions. See Maschmeyer, T., et al., Adv. Synth. Catal. No. 10, 344, 1037-1057 (2002), the disclosure of which is incorporated in its entirety by reference herein. During the reductive amination of the second portion of hydroxyacetone, the reaction between the hydroxyacetone and the amine compound results in the formation of the adduct (148). In one embodiment, hydroxyacetone may be added gradually to the amine compound in order to maintain low concentrations of hydroxyacetone in the reaction mixture. Also, one skilled in the art would recognize that the reductive amination may be optionally carried out in a single reactor, such as the second reactor (150), by adding the hydroxyacetone, amine compound, and reducing agent (such as a hydrogenation catalyst and hydrogen) in the same reactor.

According to various embodiments of the processes of the present disclosure, the first portion of the hydroxyacetone may be directly reduced with the reducing agent (i.e., not reacted with the amine compound). According to these embodiments, the first portion of hydroxyacetone does not react with the amine compound when the hydroxyacetone in the hydroxyacetone feed stream (such as 116, 130, or 134) is contacted with the amine compound (wherein, the second portion of the hydroxyacetone may react with the amine compound, as described herein). In those embodiments, where the hydroxyacetone and the amine compound are contacted outside of reactor (150), the unreacted first portion of hydroxyacetone may be transmitted (along with the adduct (148) or the second portion of hydroxyacetone and the amine compound) to the second reactor (150). As previously mentioned, according to these embodiments direct reduction of the first portion of the hydroxyacetone will result in the production of propylene glycol (170).

According to various embodiment, the process described herein comprises reducing the hydroxyacetone (134) and the adduct (148) using a reducing agent (152) to obtain a product mixture comprising propylene glycol when the hydroxyacetone is reduced with the reducing agent and the amino alcohol product when the adduct is reduced with the reducing agent. In other words, the first portion of the hydroxyacetone in the feed (such as 116, 130 or 134) from the first reactor (110) is directly reduced with the reducing agent (152)(i.e., the first portion is not reacted with the amine compound (144) to produce the adduct (148)) in the second reactor (150) to produce the propylene glycol (170) in the product mixture and the second portion of the hydroxyacetone (116, 130, or 134) in the feed from the first reactor is converted to the adduct (148)(via reaction with the amine compound (144)) and the adduct is reduced in the second reactor (150) with the reducing agent (152) to produce the amino alcohol product (180) in the product mixture.

The process for reducing the hydroxyacetone and the adduct will now be described in greater detail. The resulting adduct (148) and the hydroxyacetone (134) may be added to the second reactor (150) and reduced with a reducing agent (152) to produce a product mixture comprising an amino alcohol product (180) and propylene glycol (170), respectively. In certain embodiments, the reducing agent may be any reducing agent known in the art. For example, suitable reduction reactions include hydrogenation with hydrogen gas and a hydrogenation catalyst, reduction with a hydride source (such as, but not limited to, sodium borohydride, acyloxyborohydrides, triacetoxy borohydride, cyanoborohydrides, and the like), dissolving metal reductions, and aluminum-mercury amalgam reductions. In certain embodiments, the reducing agent (152) may comprise hydrogen gas in the presence of a hydrogenation catalyst, such as a metal hydrogenation catalyst, selected from the group consisting of nickel, cobalt, RANEYO nickel, RANEY® cobalt, RANEY® nickel or RANEY® cobalt doped with other transition metals, nickel oxide, copper, palladium, platinum, rhodium, ruthenium, chromium, iridium, rhenium, molybdenum, iron, manganese, titanium, zirconium, magnesium, oxides thereof, and combinations of any thereof. In specific embodiments, the hydrogenation catalyst may be RANEY® nickel, RANEY® cobalt, or combinations thereof. In certain embodiments, the hydrogenation catalyst may be supported on a material selected from the group consisting of alumina, titania, zirconia, charcoal, chromia, silica, zeolites and combinations of any thereof. The hydrogenation catalyst may be soluble or insoluble and may be dissolved into the reaction mixture or located inside the second reactor (150) as a slurry or packed bed. Although the amount of the hydrogenation catalyst used may vary, in certain embodiments from about 0.01% to about 100% of catalyst may be used and in other embodiment from about 1% to about 20% of catalyst may be used, on a dry weight basis relative to the hydroxyacetone or the adduct, for example in a slurry type reactor. For other reactors, such as continuous reactor, for example a fixed bed reactor (including trickle bed reactors), the catalyst loading of the reactor may vary and may depend on the bed reactor design, such as the bed volume of the reactor and/or the reactant flow rate.

According to certain embodiments where the reducing agent comprises hydrogen and a hydrogenation catalyst, reacting the hydroxyacetone may comprise adding the hydroxyacetone (such as 116, 130, or 134), the amine compound (144) and the hydrogen to a reactor, such as the second reactor (150), wherein the reactor contains the hydrogenation catalyst. For example, the reactor may be a fixed bed reactor, such as a trickle bed reactor (as described herein) and a first portion of the hydroxyacetone may be directly reduced in the reactor by the hydrogen and the reducing agent to produce propylene glycol (170), and a second portion of the hydroxyacetone may be reacted with the amine compound (144) in the reactor to produce the adduct (148) and the adduct may be reduced in the reactor by the hydrogen and the reducing agent to produce the amino alcohol compound (180). In a specific embodiment, the amine compound and the hydrogen may be added to the reactor as a gaseous mixture, for example, where the amine compound comprises ammonia. In another embodiment, the amine compound and the hydrogen may be added to the reactor separately.

According to various embodiments, the reaction conditions at which the hydroxyacetone (such as 116, 130, or 134) and the adduct (148) can be reduced by the reducing agent (152) may differ. For example, in certain embodiment where the reducing agent (152) comprises hydrogen and the hydrogenation catalyst, the hydrogen may be at a partial pressure of from about 1 bar to about 350 bar, and in other embodiments the hydrogen may be at a partial pressure of from about 10 bar to about 150 bar. According to certain embodiments, the reduction may be carried out at a temperature ranging from about 20° C. to about 250° C. and in other embodiments from about 40° C. to about 85° C. The reaction time may also vary depending on the reducing agent and/or reaction conditions. For example, in certain embodiments, reducing the hydroxyacetone and the adduct may occur over from about 1 minute to about 24 hours, and in other embodiments from about 30 minutes to about 6 hours.

According to certain embodiments, reducing the hydroxyacetone and the adduct using the reducing agent to obtain a product occurs in a reactor, such as the second reactor (150) selected from the group consisting of a batch reactor, a stirred tank reactor, a semi-batch reactor, a continuous reactor, a continuous stirred tank reactor, a slurry reactor, a fixed bed reactor, a tubular reactor, a column reactor, a packed bed reactor, a fluidized bed reactor, a trickle bed reactor, a membrane reactor, a plate and frame reactor, a Carberry-type reactor, a plug flow reactor, and a reactive distillation, or various combinations of any thereof. It will be understood that the manner in which the hydroxyacetone, amine compound or adduct and reducing agent (such as the hydrogen gas and the hydrogenation catalyst) are fed/added into the reactor can vary depending on the equipment used and the phase of each reaction component.

In one embodiment, the second reactor is a trickle bed reactor. As described herein, in the trickle bed reactor the feed stream (such as the hydroxyacetone feed stream, the adduct feed stream, the amine compound feed and/or the hydrogen feed) is fed into the column at low flow so that a thin layer of the liquid forms over at least a portion of the surface of the hydrogenation catalyst particles (or hydrogenation catalyst on the surface of the support material). When the reducing process is a hydrogenation process, the space between the particles may be fed with the hydrogen gas. In other embodiments, where reacting the hydroxyacetone with the amine compound occurs in the trickle bed reactor, the amine compound may also be a gas that fills the space between the particles as a mixture with the hydrogen gas. While not intending to be limited by any particular mechanism, it is believed that the distance that the hydrogen molecules need to travel from the gas phase to the catalyst surface is through the thin layer of liquid, resulting in efficient mass transfer and an increased reaction rate as compared to other reactor set-ups. When the amine compound is added to the reactor as a gas, the amine compound may travel from the gas phase into the thin layer of liquid hydroxyacetone and react with the second portion of the hydroxyacetone to form the adduct, which may then be reduced by the hydrogen and the hydrogenation catalyst (whereas the first portion of the hydroxyacetone may be directly reduced by the hydrogen and hydrogenation catalyst). The trickle bed reactor may comprise at least one packed column, wherein the column is packed with the hydrogenation catalyst. In certain embodiments, the trickle bed reactor may comprise a plurality of columns packed with the hydrogenation catalyst, such as, for example, from 2 to 10 columns, arranged in series or in parallel. One skilled in the art would recognize that the number of columns in the trickle bed reactor may vary according to the required reaction time, the flow rate of the process, and/or the height, total bed volume, or catalyst loading of the column.

According to certain embodiments, at least one of the first reactor (110) and the second reactor (150) may be a trickle bed reactor. According to other embodiments, each of the first reactor (110) and the second reactor (150) are trickle bed reactors. In still another embodiment, the first reactor (110) and the second reactor (150) are the same reactor.

According to various embodiments of the processes disclosed herein, the ratio of the propylene glycol and the amino alcohol product in the product mixture may be varied by changing one or more variable in the process. Thus, in certain embodiments, the ratio of propylene glycol and amino alcohol product in the product mixture may be controlled by the user of the process according to the desired product ratio. For example, according to certain embodiments, the ratio of propylene glycol and the amino alcohol product in the product mixture may be determined by a factor selected from the group consisting of the reaction rate of hydroxyacetone with the amine compound; the reaction rate of the hydroxyacetone with the reducing agent; the temperature of the reaction of the hydroxyacetone with the reducing agent or the amine compound; the partial pressure of the amine compound; the reactivity of the reducing agent; the mass transfer of reactants in a reactor; the molar ratio of the amine compound and the reducing agent; the molar ratio of hydroxyacetone to the amine compound; the residence time of the reactants in the reactor; and combinations of any thereof.

For example, the ratio of products in the product mixture may be determined by the reaction rates of the hydroxyacetone with the amine compound and the reducing agent, particularly if both reactions occur concurrently. That is, if the rate of reaction between the hydroxyacetone and the amine compound is faster than that of hydroxyacetone with the reducing agent, then more hydroxyacetone will react with the amine compound over a given time and the product mixture will comprise a greater ratio of amino alcohol product compared to propylene glycol. However, if the rate of reaction between the hydroxyacetone and the amine compound is slower than that of hydroxyacetone with the reducing agent, then less hydroxyacetone will react with the amine compound over a given time and the product mixture will comprise a greater ratio of propylene glycol compared to amino alcohol product. Alternatively, if the amine compound is added to the hydroxyacetone stream prior to the second reactor (as described herein), then the ratio of amino alcohol product to propylene glycol may depend on the reaction rate of the hydroxyacetone with the amine compound and the length of time the two components are in contact prior to contacting the reducing agent.

Further, the ratio of products in the product mixture may be determined by the temperature of the reaction of the hydroxyacetone with the reducing agent or the amine compound. For example, a higher reaction temperature or lower reaction temperature may increase or decrease, respectively, the reaction rate of one reaction process relative to another. In another embodiment where the amine compound is a gas, the ratio of the product mixture may be determined by the partial pressure of the amine compound. A higher partial pressure may result in a higher reaction rate between the hydroxyacetone and the amine compound, whereas a lower partial pressure may result in a slower reaction rate.

The ratio of products in the product mixture may also be determined by the reactivity of the reducing agent, such as the reactivity of the reducing agent with hydroxyacetone compared to the reactivity of the reducing agent with the adduct. Further, where the reducing agent comprises hydrogen gas and a hydrogenation catalyst, the reactivity of the catalyst (and therefore the product ratio) may be controlled by, for example, but not limited to, changing (increasing or decreasing) the partial pressure of the hydrogen gas in the reactor, the catalyst concentration (such as the concentration of the catalyst on the solid support), selection of hydrogenation catalyst, and/or poisoning of the catalyst, such as selective poisoning of the catalyst.

Other factors that may determine the ratio of products in the product mixture may include the molar ratio of the amine compound and the reducing agent (such as the hydrogen gas or hydrogenation catalyst) and the molar ratio of hydroxyacetone to the amine compound. For example, changes in the molar ratio of the amine compound and the reducing agent, such as increasing the amount of the reducing agent, relative to the amine compound, may increase the rate of the direct reduction of hydroxyacetone to propylene glycol, thereby increasing the ratio of propylene glycol and amino alcohol in the product mixture. Increasing the molar ratio of the amine compound may increase the amount of adduct formed and consequently decrease the ratio of propylene glycol to the amino alcohol in the product mixture. Similarly, changes in the molar ratio of the hydroxyacetone to the amine compound may change the ratio of products in the product mixture. For example, increasing the ratio of hydroxyacetone to amine compound may increase the ratio of propylene glycol to the amino alcohol compound, whereas increasing the amine compound may increase the production of the amino alcohol product in the reaction mixture.

Also, changes in the residence time of one or more reactants within a reactor, such as for example the first reactor and/or the second reactor may affect the product ratio in the product mixture. For example, one or more of the products may not be stable to the conditions within the reactor for extended periods of time. Thus, as the residence time within the reactor increase, the amount of the unstable product (or intermediate that produces the unstable product) may decrease, thereby changing the ratio of products.

According to certain embodiments, the processes of the present disclosure may further comprise separating at least one of the propylene glycol and the amino alcohol product from the product mixture. For example, once the product mixture, that is, the propylene glycol (170) and the amino alcohol product (180), is obtained the various components of the product, as well as the reducing agent, may optionally be further separated from one another in one or more separation processes using any appropriate method known to those skilled in the art. For instance (referring again to FIG. 1), the reducing agent may be optionally separated (156) from the product and recycled back (158) into the second reactor (150) for reuse. In those embodiments where the reducing agent comprises hydrogen in the presence of the hydrogenation catalyst, the hydrogen may be further separated from the hydrogenation catalyst and both the unreacted hydrogen and the hydrogenation catalyst may be recycled back for reuse in later processes (not shown).

Likewise, the product may be separated in a separation process (160) so as to obtain the individual products (i.e. unreacted hydroxyacetone (161), unreacted adduct (162), unreacted amine compound (166), impurities (168), water (169) and the propylene glycol (170) and the amino alcohol product (180)). For example, streams of unreacted hydroxyacetone (161) or unreacted adduct (162) and unreacted amine (166) may be recycled for reuse to save on raw material costs. Water (168), impurities (169) and other incidental products may be considered byproducts of the reaction and, thus, can be separated and removed from the other reaction products and either processed for further use in another application, or disposed (water and impurities). The separation process (160) may include any separation process known in the art, such as, but not limited to, flash distillation, fractional distillation, chromatography, extraction, passing through an acidic resin, and combinations of any thereof. Finally, the product, i.e., the propylene glycol (170) or the amino alcohol product (180) may be collected as the desired product for use in a variety of application. In certain embodiments, the process may further comprise separating at least one of the propylene glycol and the amino alcohol product from the product mixture. The propylene glycol and the amino alcohol product in the product mixture may be separated by a process selected from the group consisting of flash distilling the product mixture, fractionally distilling the product mixture, winterizing the product mixture, passing the product mixture through an acidic resin and combinations of any thereof. For example but not intending to limit the use of the products, the amino alcohol product (180) may be used as solvents, intermediates for making surface active agents, corrosion inhibitors in metal working fluids, neutralizing agents in acid scrubbing during natural gas or syngas purification processes, and aids in the preparation of compounds in the pharmaceutical industry. Propylene glycol (170) produced from the process may be used, for example, but not limited to, as functional fluids, such as aircraft de-icing fluids, antifreezes, lubricants, inks, and heat transfer fluids, paints and coatings, plasticizers, and cellophane, as well as in cosmetics, personal care products, pharmaceuticals, and food applications. It should be noted that in those embodiments where the glycerol reactant was derived from biological sources, such as, for example, hydrolysis of triglyceride fats and oils, the propylene glycol or amino alcohol product will be a bioderived product from a renewable resource. As will be understood by those skilled in the art, the specific separation processes used and the degree of separation may depend on the desired purity of the reaction products.

Alternatively, the product mixture comprising the propylene glycol and the amino alcohol product may be used directly in certain industrial processes or commercial applications. In other embodiments, the product mixture may be purified, for example by one or more separation processes described herein, to remove at least one of unreacted hydroxyacetone (161), unreacted adduct (162), unreacted amine compound (166), impurities (168), and/or water (169), and the purified product mixture comprising propylene glycol and the amino alcohol product may then be used in certain industrial processes or commercial applications.

The amino alcohol product produced in the processes described herein may be a 2-amino-1-propanol. Certain embodiments of the present disclosure may include a process for converting glycerol to a product mixture comprising propylene glycol and a 2-amino-1-propanol comprising reacting glycerol with a metal catalyst in a first reactor to obtain hydroxyacetone and reacting the hydroxyacetone with a reducing agent or an amine compound and the reducing agent to obtain a product mixture comprising propylene glycol and a 2-amino-1-propanol. Reacting the hydroxyacetone may comprise reducing a first portion of the hydroxyacetone in a reactor with the reducing agent to produce the propylene glycol in the product mixture and reacting a second portion of the hydroxyacetone with an amine compound to produce an adduct and reducing the adduct with the reducing agent to produce the 2-amino-1-propanol in the product mixture. Various embodiments of the elements of the processes are described in greater detail herein.

In certain embodiments, the amino alcohol product may be a 2-amino-1-propanol having the general formula:

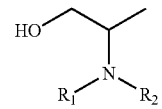

where $R_1$ and $R_2$ are independent of one another and are selected from the group consisting of H, straight-chain or branched-chain $C_1$-$C_{20}$ alkyl (such as methyl, ethyl, n-proyl, isopropyl, n-butyl, isobutyl, sec-butyl, t-butyl, n-pentyl, iso-pentyl, sec-pentyl, neopentyl, n-hexyl, n-heptyl, n-octyl, 2-ethyl hexyl, n-decyl, n-dodecyl, 2-butyloctyl, n-tridecyl, n-tetradecyl), $C_3$-$C_{20}$ cycloalkyl (for example, $C_3$-$C_8$-cycloalkyl such as cyclopropyl, cyclobutyl, cyclopentyl, cyclohexyl, cycloheptyl, and cyclooctyl), $C_1$-$C_{20}$ hydroxyalkyl (such as 2-hydroxyethyl, 2-hydroxy-n-propyl, 3-hydroxy-n-propyl, 1-hydroxy-methyl-ethyl), aryl (such as phenyl, 1-naphthyl, 2-naphthyl, 1-anthryl, 2-anthryl, and 9-anthryl), $C_7$-$C_{20}$-alkyl-aryl (such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2-ethylphenyl, 3-ethylphenyl, 4-ethylphenyl, 2-n-propylphenyl, 3-n-propylphenyl, 4-n-propylphenyl), $C_7$-$C_{20}$-arylalkyl (such as benzyl, 1-phenethyl, 2-phenetyl, 1-phenylpropyl, 2-phenylpropyl, 3-phenylpropyl, 1-phenylbutyl, 2-phenylbutyl, 3-phenylbutyl, 4-phenylbutyl) and mixtures of any thereof. In other embodiments, $R_1$ and $R_2$ may come together to form a heterocyclic ring having from 5 to 7 ring atoms including the nitrogen atom. In view of the processes described herein, one skilled in the art would understand that other structures for groups $R_1$ and $R_2$ are possible depending on the structure of the amine compound used in the optional step of the processes and would be within the scope of the present disclosure as set forth in the claims.

In view of the above, it will be understood that embodiments of the present processes may be carried out using either semi-batch, or continuous mode.

Figure 2:
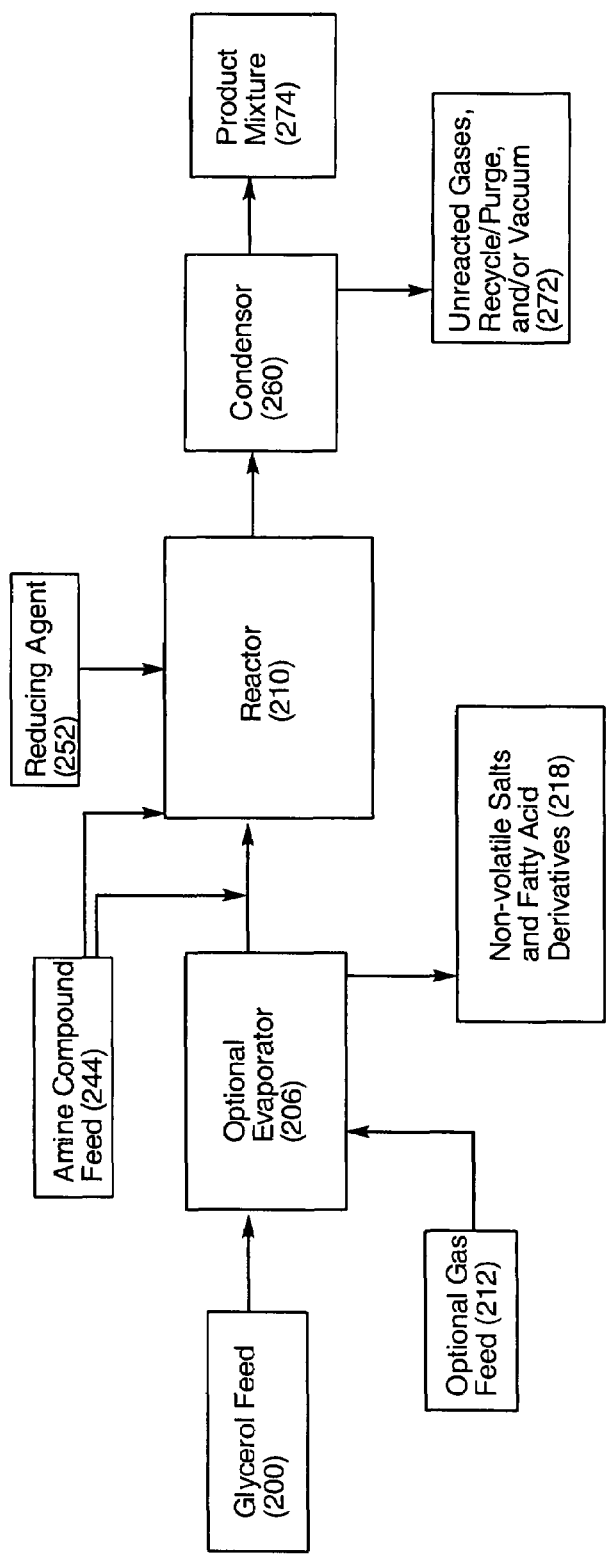
FIG. 2 illustrates a schematic flowchart representing an exemplary embodiment of a one stage process in accordance with the present disclosure.

While certain embodiments of the present disclosure may be described as a two stage process involving a first reactor and a second reactor, according to other embodiments the processes may be conducted utilizing a single reactor, for example in a one stage process. The reactor may be any of the reactor types described herein. In certain embodiments, the reactor may be a trickle bed reactor. Turning now to FIG. 2, wherein the glycerol (200) and optional gas stream (212) are fed to reactor (210). As described herein, the glycerol (200) may be a crude glycerol, a treated glycerol, or a refined glycerol. These two streams can optionally pass through evaporator (206) before being fed into reactor (210). Evaporator (206) can remove non-volatile compounds (218). The amine compound (244) is fed either directly into reactor (210) or mixed with the other reactants (200, 212) before entering reactor (210). The reaction from glycerol to hydroxyacetone to the product mixture comprising the amino alcohol and propylene glycol occurs in reactor (210). The reacted mixture is fed to a condenser (260) wherein the desired product mixture (274) comprising the amino alcohol and the propylene glycol is separated from the unreacted gasses and other by-products (272). The feed streams (200, 212, and 244) are the same as those described above with respect to the two stage process of FIG. 1. In certain embodiments, where the amine compound is a gas, such as gaseous ammonia, the amine compound may serve the purpose of gas (212). In other embodiments where the reducing agent (252) is hydrogen and a hydrogenation catalyst, the hydrogen gas may serve the purpose of gas (212). In other embodiments, gas (212) may be a mixture of gas, including a gaseous amine and/or hydrogen. Likewise, the equipment used (206, 210 and 260) can be any of the evaporators, reactors, and condensers described herein. In certain embodiments, the reactor may be a fixed bed reactor, such as a trickle bed reactor, as described herein. In certain embodiment, the fixed bed reactor may contain or be packed with a mixture of the metal catalyst and the hydrogenation catalyst (as described herein). In other embodiments, the metal catalyst and the hydrogenation catalyst may be the same.

The following representative examples are included for purposes of illustration and not limitation.

EXAMPLES

Example 1

About 300 g of refined glycerol (Superol Brand, P&G Chemicals, USA) and about 8.5 g of copper-chromite catalyst (CU-1886P, Engelhard, USA) were weighed out and transferred into a 500 mL reaction flask equipped with a mechanical stirrer, thermocouple, Dean Stark trap/condenser, and gas inlet. The glassware was assembled so that the volatile hydroxyacetone was removed from the reactor as it formed (i.e. $N_2$ gas sparging) and such that samples could be collected as a function of time for later analysis. The reaction components were heated to about 230° C. with constant stirring at about atmospheric pressure. Samples of the resulting hydroxyacetone product were analyzed on an Agilent 6890N Gas Chromatogram using a SPB-1701 30 m×25 mm I.D.× 0.25 μm film column (Supelco). Standards of propylene glycol and hydroxyacetone were used as reference standards. The samples were also analyzed for water content using a model V-200 AquaStar Karl Fisher (EMScience) auto-titrator (freshly calibrated against water). About 238.6 g of hydroxyacetone product was obtained, which contained about 65.9% hydroxyacetone and about 21.7% water. Separation was carried out using fractional distillation under vacuum to yield about 155 g of 90% hydroxyacetone. About 43 g of the hydroxyacetone was charged to a flask and cooled to about 0° C. About 120 mL of 30% aqueous ammonium hydroxide was added to the hydroxyacetone dropwise with stirring while the reaction temperature was maintained below about 10° C. The mixture was stirred for about 60-90 minutes and reaction progress was monitored by gas chromatography. The resulting adduct was charged to a 300 mL Parr reactor along with about 5 g of a nickel catalyst (Actimet M, Engelhard, USA). The reactor was flushed with hydrogen gas, pressurized to about 1100 psig and heated to about 85° C. Reaction progress was monitored at various time points by using an Agilent 6890N Gas Chromatogram using a SPB-1701 30 m×25 mm I.D.×0.25 cm film column (Supelco). Standards of propylene glycol, hydroxyacetone, and 2-amino-1-propanol were run for reference purposes. The reactor was cooled to ambient temperature and the nickel catalyst was separated via filtration to yield about 71.5% of 2-amino-1-propanol.

Example 2

About 375 g of treated glycerol (96% glycerol, P&G Chemicals, USA) and about 11.25 g of copper-chromite catalyst (CU-1886P, Engelhard, USA) were weighed out and transferred into a 500 mL reaction flask equipped with a mechanical stirrer, thermocouple, Dean Stark trap/condenser, and gas inlet. The glassware was assembled so that the volatile hydroxyacetone was removed from the reactor as it formed (i.e. $N_2$ gas sparging). The reaction components were heated to about 230° C. with constant stirring at about atmospheric pressure. Samples of the resulting hydroxyacetone product were collected and analyzed as described in Example 1. About 274.9 g of the hydroxyacetone product (containing about 63.7% hydroxyacetone) was obtained and separated by distillation. About 43 g of the resulting hydroxyacetone (having about 90% purity) was charged to a flask at a temperature of about 10° C. About 120 mL of 30% aqueous ammonium hydroxide was added dropwise with stirring while the reaction temperature is maintained at about 10° C. The mixture was stirred for about 60-90 minutes and reaction progress was monitored by gas chromatography. The resulting adduct was then charged to a 300 mL Parr reactor along with about 10 g of nickel catalyst (Actimet M, Engelhard, USA). The reactor was flushed with hydrogen gas, pressurized to about 1100 psig and heated to about 85° C. Reaction progress was monitored by gas chromatography as described in Example 1. The reactor was cooled to about ambient temperature and the nickel catalyst was separated from the amino alcohol product via filtration to yield about 84.6% of 2-amino-1-propanol.

Example 3

About 88 g of crude glycerol (88.7% glycerol, Twin Rivers Technologies, USA) was flashed over into a 500 mL reaction flask equipped with a mechanical stirrer, thermocouple, Dean Stark trap/condenser, and gas inlet. About 9 g of copper-chromite catalyst (CU-1886P, Engelhard, USA) was added to the reactor. The glassware was assembled so that the volatile hydroxyacetone was removed from the reactor as it formed (i.e. $N_2$ gas sparging). Samples of the resulting hydroxyacetone product were collected and analyzed as described in Example 1. About 207.9 g of the hydroxyacetone product (containing about 49.8% hydroxyacetone) was obtained. About 50 g of the hydroxyacetone product was then charged to a flask and about 61 mL of 30% aqueous ammonium hydroxide was added dropwise with stirring at about room temperature. The mixture was stirred for about 90 minutes and reaction progress was monitored using gas chromatography. The resulting adduct was charged to a 300 mL Parr reactor along with about 6 g of a nickel catalyst (Actimet M, Engelhard, USA). The reactor was flushed with hydrogen gas, pressurized to about 1100 psig and heated to a temperature of about 85° C. Reaction progress was monitored by gas chromatography as described in Example 1. The reactor was cooled to ambient temperature and the nickel catalyst was separated from the resulting amino alcohol product via filtration to yield about 83.5% of 2-amino-1-propanol.

Example 4

About 299 g of refined glycerol (Superol Brand, P&G Chemicals, USA) and about 8.5 g of copper-chromite catalyst (CU-1955P, Engelhard, USA) were weighed out and transferred into a 500 mL reaction flask. The flask was equipped with a mechanical stirrer, thermocouple, Dean Stark trap/condenser, and gas inlet. The glassware was assembled so that the volatile hydroxyacetone was removed from the reactor as it formed (i.e. $N_2$ gas sparging is used). Samples of the resulting hydroxyacetone product were collected and analyzed as described in Example 1. About 235 g of the hydroxyacetone product was obtained and was determined to contain about 59.4% hydroxyacetone. The hydroxyacetone product was separated using fractional distillation under vacuum to yield about 150 g of 90% hydroxyacetone, about 95 g of which was then charged to a flask. Ammonia gas (Mattheson Tri Gas, USA) was slowly bubbled through the hydroxyacetone for about 30 minutes while keeping the temperature at or below about 20° C., followed by stirring for an additional 30 minutes. Reaction progress was monitored by gas chromatography. The resulting adduct was charged to a 300 mL Parr reactor along with about 18 g of a nickel catalyst (Actimet M, Engelhard, USA). The reactor was flushed with hydrogen gas, pressurized to about 1100 psig and heated to a temperature of about 85° C. Reaction progress was monitored by gas chromatography as described in Example 1. The reactor was cooled to ambient temperature and the nickel catalyst was separated from the resulting amino alcohol product via filtration to yield about 33.4% of 2-amino-1-propanol.

Example 5

In this Example, hydroxyacetone was converted to 2-amino-1-propanol using a nickel oxide hydrogenation catalyst. Hydroxyacetone (36.71 g, 0.50 mol) was charged to a 250 mL round bottom flask at room temperature. Ammonium hydroxide (100 mL, 1.48 mol) was dropwise added with stirring. The reaction was stirred for a total time of 90 minutes. Progress was monitored by GC. The resulting adduct solution was charged to a 300 mL Parr reactor along with nickel oxide on kieselguhr (Sud-Chemie, G-49B RS: 1.52 g, 1.1 wt %). The reactor was flushed four times with $H_2$, pressurized with $H_2$ to 151.7 bar, and heated to 85° C. with stirring at 1500 rpm using a gas entrainment impeller. Reaction progress was monitored by gas chromatography as described in Example 1. The reactor was cooled to ambient temperature and the catalyst was separated via filtration to yield 2-amino-1-propanol with a conversion of 96% and a selectivity of 98%.

Example 6

In this Example, hydroxyacetone was converted to 2-amino-1-propanol using a nickel oxide hydrogenation catalyst at lower hydrogen pressure. Hydroxyacetone (36.92 g, 0.50 mol) was charged to a 250 mL round bottom flask at room temperature. Ammonium hydroxide (100 mL, 1.48 mol) was dropwise added with stirring. The reaction was stirred for a total time of 90 minutes. Progress was monitored by GC. The resulting adduct solution was charged to a 300 mL Parr reactor along with nickel oxide on kieselguhr (Sud-Chemie, G-49B RS: 1.55 g, 1.1 wt %). The reactor was flushed four times with $H_2$, pressurized with $H_2$ to 34.5 bar, and heated to 85° C. with stirring at 1500 rpm using a gas entrainment impeller. Reaction progress was monitored by gas chromatography as described in Example 1. The reactor was cooled to ambient temperature and the catalyst was separated via filtration to yield 2-amino-1-propanol with a conversion of 92% and a selectivity of 73%.

Example 7

In this Example, hydroxyacetone was converted to a product mixture comprising propylene glycol and 2-amino-1-propanol in a batch-type process. Hydroxyacetone (98.91 g, 1.34 mol) was charged to a 250 mL round bottom flask at room temperature. Ammonium hydroxide (46.0 mL, 0.68 mol) was dropwise added with stirring. The reaction was stirred for a total time of 90 minutes. Progress was monitored by GC. The resulting adduct solution was charged to a 300 mL Parr reactor along about 5 g of a nickel catalyst (Actimet M, Engelhard, USA). The reactor was flushed with $H_2$, pressurized with $H_2$ to 151.7 bar and heated to 85° C. with stirring at 1500 rpm using a gas entrainment impeller. Reaction progress was monitored by gas chromatography as described in Example 1. The reactor was cooled to ambient temperature and the catalyst was separated via filtration to yield a product mixture comprising 2-amino-1-propanol (17.9%) and propylene glycol (30.7%).

Example 8

In this Example, hydroxyacetone was converted to propylene glycol in a batch-type process. Crude hydroxyacetone, 70 g, (obtained as described in Example 1) was charged to a 300 mL Parr reactor along 0.5 g of a Ru/C catalyst (Aldrich Chemicals, Milwaukee, Wis.). The reactor was flushed with $H_2$ several times, pressurized with $H_2$ to 10.3 bar and heated to 120° C. under vigorous stirring for 3 hrs. The reactor was then cooled to ambient temperature and the catalyst was separated via filtration to yield the product mixture with a composition according to Table 1.

TABLE 1

| Product Mixture from Reduction of Hydroxyacetone | | |
|---|---|---|
| Wt. % Component | Crude Hydroxyacetone | Reaction Product |
| Hydroxyacetone | 63.9 | 4.0 |
| Propylene Glycol | 3.0 | 67.6 |
| Water | 19.6 | 21.6 |
| Glycerol | 1.2 | 3.1 |
| By-Products | 12.3 | 3.8 |

Example 9

In this Example, glycerol was converted to propylene glycol via a single stage (on reactor) reaction. Glycerol (100 g, 1.1 mol) was charged to a 300 mL Parr reactor along 5 g of a copper chromite catalyst (CU-1886P, Engelhard, USA). The reactor was flushed with $H_2$ several times, pressurized with $H_2$ to 103.4 bar, and heated to 230° C. with stirring at 550 rpm. Reaction progress was monitored by gas chromatography. After 21 hrs, the reactor was cooled to ambient temperature and the catalyst was separated via filtration to yield a product mixture containing 55% glycerol, 35% propylene glycol, 3.9% propanol, and other impurities such as ethylene glycol, methanol, and ethanol.

Example 10

In this Example, hydroxyacetone was reacted with ammonium hydroxide to give the adduct which was converted to 2-amino-1-propanol using a trickle bed reactor. Hydroxyacetone (37.33 g, 0.50 mol) was charged to a 250 mL round bottom flask at room temperature. Ammonium hydroxide (100 mL, 1.48 mol) was dropwise added with stirring. The reaction was stirred for a total time of 90 minutes. Progress was monitored by GC. The adduct was submitted to the trickle bed reactor.

A trickle bed reactor with a length of 37.9 cm and an internal diameter 2.54 cm was used. The adduct solution was fed to the reactor via an HPLC pump. The catalyst used was a RANEY® Nickel catalyst (Raney 5886, commercially available from GRACE Davison) supplied in the form of particles. The $H_2$ pressure in the reactor was 31.0 bar. The reaction was conducted in three runs changing the residence time in the reactor, the hydrogen:adduct ratio, the feed flow rate and the gas flow rate. The conditions for each run are presented in Table 2. Product samples from the reactor were condensed and were analyzed on a Agilent 6890N Gas Chromatogram using a SPB-1701 30 m×25mm I.D.×0.25 μm film column (available from Supelco). The results of the three runs are presented in Table 3.

TABLE 2

| Reaction Conditions | | | |
|---|---|---|---|
| Example | 10.1 | 10.2 | 10.3 |
| Inlet Temperature ° C. | 85 | 85 | 85 |
| Column Temperature ° C. | 85 | 85 | 85 |
| Pressure, bar | 31.0 | 31.0 | 31.0 |
| Residence Time, s | 1200 | 2400 | 600 |
| Hydrogen: Adduct ratio | 8 | 16 | 16 |
| Feed Flow Rate (mL/min) | 0.5 | 0.25 | 1.0 |
| Gas Flow Rate (sccm) | 49.8 | 49.8 | 102.6 |

TABLE 3

| Results for Trickle Bed Production of 2-Amino-1-Propanol | | | |
|---|---|---|---|
| Example | 10.1 | 10.2 | 10.3 |
| % Adduct | 38.9 | 25.1 | 63.4 |
| % 2-Amino-1-propanol | 58.8 | 60.8 | 29.7 |
| % Hydroxyacetone | 2.3 | 3.6 | 2.9 |
| % Propylene glycol | 0 | 0 | 0 |
| % Other | 0 | 10.5 | 4 |

Example 11

In this Example a trickle bed reactor is used to convert hydroxyacetone to propylene glycol. A trickle bed reactor with a length of 37.9 cm and an internal diameter of 2.54 cm is used. A hydroxyacetone solution containing 20 wt. % water is fed to the reactor via an HPLC pump. The catalyst used is a Raney Nickel catalyst (Raney 5886, commercially available from GRACE Davison) supplied in the form of particles. Reaction conditions used are presented in Table 4. Product samples from the reactor are condensed and are analyzed on a Agilent 6890N Gas Chromatogram using a DB-1 25 m×0.53 mm I.D.×5.00 micron column (available from J & W Scientific. Catalog # 1251025).

Analysis of the organic constituents by GC of the reaction product shows a mixture comprising propylene glycol, hydroxyacetone, and water. The water and hydroxyacetone are evaporated from the product using a laboratory rotary vacuum dryer, leaving a final product comprising propylene glycol.

TABLE 4

| Reaction Conditions | |
|---|---|
| Feed | Purified Hydroxyacetone (>99%) |
| Pressure | about 31.0 bar |
| Temperature | about 85° C. |
| Hydrogen Flow Rate | about 90 sccm |
| Ammonia Flow Rate | about 10 sccm |
| Feed Flow Rate | about 0.5 mL/min |

Example 12

In this Example, a trickle bed reactor is used to convert hydroxyacetone to a product mixture comprising propylene glycol and 2-amino-1-propanol via the adduct intermediate. A trickle bed reactor with a length of 37.94 cm and an internal diameter of 2.54 cm and containing about 190 cc of catalyst is prepared. The catalyst is a RANEY® Nickel catalyst (Raney 5886, commercially available from GRACE Davison) supplied in the form of particles Hydroxyacetone solution is fed to the reactor via an HPLC pump. Product samples from the reactor were condensed and were analyzed on a Agilent 6890N Gas Chromatogram using a DB-1 25 m×0.53 mm I.D.×5.00 micron column (available from J & W Scientific. Catalog # 1251025. The reaction conditions are presented in Table 5.

TABLE 5

| Reaction Conditions | |
|---|---|
| Feed | Purified Hydroxyacetone (>99%) |
| Pressure | about 31.0 bar |
| Temperature | about 85° C. |
| Hydrogen Flow Rate | about 90 sccm |
| Ammonia Flow Rate | about 10 sccm |
| Feed Flow Rate | about 0.5 mL/min |

Analysis of the organic constituents by GC of the reaction product shows a mixture of 2-amino-1-propanol, propylene glycol, hydroxyacetone, and water. The water and hydroxyacetone are evaporated from the product using a laboratory rotary vacuum dryer, leaving a final product composed of 2-amino-1-propanol and propylene glycol.

Example 13

In this Example, glycerol was converted to propylene glycol using a trickle bed reactor. The reactor used for the continuous version of this process was a trickle bed reactor with a length of 37.94 cm and an internal diameter of 2.54 cm and containing 190 cc of catalyst. The catalyst used was a copper chromite catalyst (CU-1808 T 1/8, commercially available from Engelhard) in the form of 3.2 mm extruded pellets.

The catalyst, once loaded, was first activated by the supply of a stream of 100% nitrogen to the reactor with heating until the reactor reached the desired activation temperature of 130° C. The stream of nitrogen gas was then replaced by a stream including 98% by volume of nitrogen and 2% by volume of hydrogen, and conditions were maintained until no exotherm was noted in catalyst bed. During this operation, which lasts for several hours, it was important to prevent the temperature from exceeding 170° C. The hydrogen was incrementally increased (2, 5, 10, 25, 50, 100%) until the stream was solely hydrogen.

Fifteen runs were conducted while varying the reaction conditions (temperature, glycerol flow rate, hydrogen flow rate, molar ratio of hydrogen to glycerol, and residence time within the reactor). Reaction Conditions for the various runs are listed in Table 6. Product samples were analyzed on an Agilent 6890N Gas Chromatogram using a DB-1 25 m×0.53 mm I.D.×5.00 micron column (available from J & W Scientific. Catalog # 1251025). The compositions of the product mixture for each of the fifteen runs are listed in Table 7.

TABLE 6

Reaction Conditions

| Run # | Temp (° C.) | Pressure (bar) | Glycerol Flow Rate (mL/min) | H$_2$ Flow Rate (sccm) | Mole Ratio (H$_2$:Gly) | Residence Time (min) |
|---|---|---|---|---|---|---|
| 1 | 200 | 32.0 | 0.5 | 36 | 4 to 1 | 15 m |
| 2 | 200 | 32.0 | 0.5 | 178.3 | 20 to 1 | 15 m |
| 3 | 200 | 32.0 | 0.5 | 356.5 | 40 to 1 | 15 m |
| 4 | 200 | 32.0 | 0.12 | 11.14 | 5 to 1 | 60 m |
| 5 | 200 | 32.0 | 0.25 | 34.3 | 10 to 1 | 30 m |
| 6 | 200 | 32.0 | 0.25 | 76.25 | 20 to 1 | 30 m |
| 7 | 200 | 32.0 | 0.5 | 73.025 | 10 to 1 | 15 m |
| 8 | 180 | 32.0 | 0.25 | 36.51 | 10 to 1 | 30 m |
| 9 | 220 | 32.0 | 0.25 | 36.51 | 10 to 1 | 30 m |
| 10 | 220 | 32.0 | 0.25 | 109.54 | 30 to 1 | 30 m |
| 11 | 180 | 32.0 | 0.75 | 36.51 | 3.33 to 1 | 10 m |
| 12 | 180 | 32.0 | 0.25 | 109.54 | 30 to 1 | 30 m |
| 13 | 220 | 32.0 | 0.75 | 36.51 | 3.33 to 1 | 10 m |
| 14 | 180 | 32.0 | 0.75 | 109.54 | 10 to 1 | 10 m |
| 15 | 220 | 32.0 | 0.75 | 109.54 | 10 to 1 | 10 m |

TABLE 7

Results for Trickle Bed Production of Propylene Glycol

| | GC Data by Wt. % | | | |
|---|---|---|---|---|
| Run # | % PG | % HA | % Gly | % Other |
| 1 | 37.8% | 1.9% | 52.8% | 7.5% |
| 2 | 41.2% | 2.8% | 44.8% | 11.2% |
| 3 | 38.8% | 2.2% | 51.2% | 7.8% |
| 4 | 62.4% | 8.9% | 18.3% | 10.4% |
| 5 | 72.4% | 5.6% | 10.3% | 11.8% |
| 6 | 62.4% | 9.2% | 19.9% | 8.5% |
| 7 | 38.9% | 1.6% | 40.3% | 19.2% |
| 8 | 35.3% | 8.4% | 29.6% | 26.6% |
| 9 | 49.6% | 6.1% | 12.8% | 31.5% |
| 10 | 45.7% | 2.9% | 22.7% | 28.7% |
| 11 | 13.0% | 2.9% | 70.1% | 13.9% |
| 12 | 26.5% | 6.6% | 24.5% | 42.4% |
| 13 | 36.8% | 5.6% | 16.2% | 41.3% |
| 14 | 11.7% | 0.8% | 76.3% | 11.3% |
| 15 | 36.0% | 3.6% | 21.9% | 38.5% |

PG = propylene glycol, HA = hydroxyacetone, Gly = glycerol

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for converting glycerol to a product mixture comprising propylene glycol and an amino alcohol product, the process comprising:
    reacting glycerol with a metal catalyst to obtain hydroxyacetone; and
    reacting the hydroxyacetone with i) a reducing agent and ii) an amine compound and a reducing agent to obtain a product mixture comprising propylene glycol and an amino alcohol product.

2. The processs of claim 1, wherein reacting the hydroxyacetone occurs in a reactor and comprises reducing a first portion of the hydroxyacetone in the reactor with the reducing agent to produce the propylene glycol in the product mixture and reacting a second portion of the hydroxyacetone with the amine compound to produce an adduct and reducing the adduct with the reducing agent in the reactor to produce the amino alcohol product in the product mixture.

3. The process of claim 1, further comprising separating at least one of the propylene glycol and the amino alcohol product from the product mixture.

4. The process of claim 3, wherein at least one of the propylene glycol and the amino alcohol product in the product mixture are separated by a process selected from the group consisting of flash distilling the product mixture, fractionally distilling the product mixture, winterizing the product mixture, passing the product mixture through an acidic resin, and combinations of any thereof.

5. The process of claim 1, wherein a ratio of the propylene glycol and the amino alcohol product in the product mixture is determined by a factor selected from the group consisting of a reaction rate of hydroxyacetone with the amine compound; a reaction rate of the hydroxyacetone with the reducing agent; a temperature of the reaction of the hydroxyacetone with the reducing agent or the amine compound; a partial pressure of the amine compound; a reactivity of the reducing agent a mass transfer of reactants in a reactor; a molar ratio of the amine compound and the reducing agent a molar ratio of hydroxyacetone to the amine compound; a residence time of the reactants in a reactor; and combinations of any thereof.

6. The process of claim 1, wherein the reacting the glycerol with the metal catalyst to obtain hydroxyacetone and reacting the hydroxyacetone with i) the reducing agent and ii) the amine compound and the reducing agent, occur in a reactor selected flow the group consisting of a batch reactor, a stirred tank reactor, a semi-batch reactor, a continuous reactor, a continuous stirred tank reactor, a slurry reactor, a fixed bed reactor, a tubular reactor, a column reactor, a packed bed reactor, a fluidized bed reactor, a trickle bed reactor, a membrane reactor, a plate and flame reactor, a Carberry-type reactor, a plug flow reactor, a reactive distillation, and combinations of any thereof.

7. The process of claim 6, wherein the reactor is a trickle bed reactor.

8. The process of claim 1, wherein reacting the glycerol with the metal catalyst to obtain hydroxyacetone occurs in a first reactor and the reacting the hydroxyacetone with i) the reducing agent and ii) the amine compound and the reducing agent, occurs in a second reactor, wherein due first reactor and the second reactor are independently selected from the group consisting of a batch reactor, a stirred tank reactor, a semi-batch reactor, a continuous reactor, a continuous stirred tank reactor, a slimy reactor, a fixed bed reactor, a tubular reactor, a column reactor, a packed bed reactor, a fluidized bed reactor, a trickle bed reactor, a membrane reactor, a plate and frame reactor, a Carberry-type reactor, a plug flow reactor, a reactive distillation, and combinations of any thereof.

9. The process of claim 8, wherein at least one of the first reactor and the second reactor is a trickle bed reactor.

10. The process of claim 1, wherein the metal catalyst is a catalyst selected from the group consisting of copper, chromium, nickel, zinc, cobalt manganese, silicon, aluminum, copper chromite, copper zinc, oxides thereof, and combinations of any thereof.

11. The process of claim 1, wherein reacting the glycerol with the metal catalyst occurs at a temperature ranging from about 160° C. to about 300° C.

12. The process of claim 1, wherein reacting the hydroxyacetone with i) the reducing agent and ii) the amine compound and the reducing agent, occurs at a temperature ranging from about 20° C. to about 250° C.

13. The process of claim 1, wherein the amine compound is a compound selected from the group consisting of ammonia, ammonium hydroxide, hydroxylamine, primary amines, secondary amines, alkanolamines, and combinations of any thereof.

14. The process of claim 1, wherein reacting the hydroxyacetone with the amine compound and the reducing agent further comprises adding an acid catalyst.

15. The process of claim 1, wherein the reducing agent comprises hydrogen and a hydrogenation catalyst selected from the group consisting of nickel, cobalt, RANEY® nickel, RANEY® cobalt, RANEY® nickel or RANEY® cobalt doped with other transition metals, nickel oxide, copper, palladium, platinum, rhodium, ruthenium, chromium, iridium, rhenium, manganese, molybdenum, iron, titanium, zirconium, magnesium, oxides thereof, and combinations of any thereof.

16. The process of claim 15, wherein the hydrogenation catalyst is supported on a material selected from the group consisting of alumina, titania, zirconia, charcoal, chromia, silica, zeolites, and combinations of any thereof.

17. The process of claim 15, wherein the hydrogen has a partial pressure ranging from about 1 bar to about 350 bar.

18. A process for convening glycerol to a product mixture comprising propylene glycol and a 2-amino-1-propanol comprising:
reacting glycerol with a metal catalyst in a first reactor to obtain hydroxyacetone; and
reacting the hydroxyacetone with i) a reducing agent and ii) an amine compound and the reducing agent,, to obtain a product mixture comprising propylene glycol and a 2-amino-1-propanol,
wherein reacting the hydroxyacetone comprises:
reducing a first portion of the hydroxyacetone in a reactor with the reducing agent to produce the propylene glycol in the product mixture; and
reacting a second portion of the hydroxyacetone with the amine compound to produce an adduct and reducing the adduct with the reducing agent in the reactor to produce the 2-amino-1-propanol in the product mixture.

19. The process of claim 18, wherein reacting the hydroxyacetone with i) the reducing agent and ii) the amine compound and the reducing agent, occurs in the first reactor.

20. The process of claim 18, wherein the first reactor is a trickle bed reactor.

21. The process of claim 18, wherein reacting the hydroxyacetone with i) the reducing agent, and ii) the amine compound and the reducing agent, occurs in a second reactor.

22. The process of claim 21, wherein at least one of the first reactor and the second reactor is a trickle bed reactor.

23. The process of claim 18, wherein a ratio of the propylene glycol and the 2-amino-1-propanol in the product mixture is determined by a factor selected from the group consisting of a reaction rats of hydroxyacetone with the amine compound; a reaction rate of the hydroxyacetone with the reducing agent; a temperature of the reaction of the hydroxyacetone with the reducing agent or the amine compound; a partial pressure of the amine compound; a reactivity of the reducing agent; a mass transfer of reactants in a reactor; a molar ratio of the amine compound and the reducing agent; a molar ratio of hydroxyacetone to the amine compound; a residence time of the reactants in a reactor; and combinations of any thereof.

24. The process of claim 18, wherein the metal catalyst is a catalyst selected from the group consisting of copper, chromium, nickel, zinc, cobalt, manganese, silicon, aluminum, copper chromite, copper zinc, oxides thereof and combinations of any thereof.

25. The process of claim 18, wherein the amine compound is a compound selected from the group consisting of ammonia, ammonium hydroxide, hydroxylamine, primary amines, secondary amines, alkanolamines, and combinations of any thereof.

26. The process of claim 18, wherein the reducing agent comprises hydrogen and a hydrogenation catalyst selected from the group consisting of nickel, cobalt, RANEY® nickel, RANEY® cobalt RANEY® nickel or RANEY® cobalt doped with other transition metals, nickel oxide, copper, palladium, platinum, rhodium, ruthenium, chromium, iridium, rhenium, manganese, molybdenum, iron, titanium, zirconium, magnesium, oxides thereof, and combinations of any thereof.

27. A process for converting glycerol to a product mixture comprising propylene glycol and an amino alcohol product having the formula;

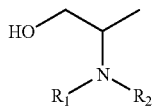

the process comprising:
reacting glycerol with a metal catalyst in a first reactor to obtain hydroxyacetone; and
reacting the hydroxyacetone with i) reducing agent and ii) an amine compound and the reducing agents to obtain a product mixture comprising propylene glycol and an amino alcohol product,
wherein reacting the hydroxyacetone comprises:
reducing a first portion of the hydroxyacetone in a reactor with the reducing agent to produce the propylene glycol in the product mixture; and
reacting a second portion of the hydroxyacetone with the amine compound to produce an adduct and reducing the adduct with the reducing agent in the reactor to produce the amino alcohol product in the product mixture, and
wherein $R_1$ and $R_2$ of the amino alcohol product are independent of one another and are selected from the group consisting of H, $C_1$-$C_{20}$ alkyl, $C_3$-$C_{20}$ cycloalkyl, $C_1$-$C_{20}$ hydroxyalkyl, aryl, $C_7$-$C_{20}$ alkyl-aryl, $C_7$-$C_{20}$ aryl-alkyl, and mixtures thereof or $R_1$ and $R_2$ come together with the nitrogen to form a heterocyclic ring having from 5 to 7 ring atoms.

28. The process of claim 27, wherein the reactor is a trickle bed reactor.

29. The process of claim 27, wherein a ratio of the propylene glycol and the amino alcohol in the product mixture is determined by a factor selected from the group consisting of a reaction rate of hydroxyacetone with the amine compound; a reaction rate of the hydroxyacetone with the reducing agent; a temperature of the reaction of the hydroxyacetone; a partial pressure of the amine compound; a reactivity of the reducing agent; a mass transfer of reactants in a reactor; a molar ratio of the amine compound and the reducing agent; a molar ratio of hydroxyacetone to the amine compound; a residence time of the reactants, in a reactor and combinations of any thereof.

* * * * *